(12) United States Patent
Jacquot et al.

(10) Patent No.: US 6,608,232 B1
(45) Date of Patent: Aug. 19, 2003

(54) METHOD FOR PREPARING A BENZYLIC-TYPE ETHER

(75) Inventors: Roland Jacquot, Francheville (FR); Michel Spagnol, Meyzieu (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/869,743

(22) PCT Filed: Jan. 7, 2000

(86) PCT No.: PCT/FR00/00024

§ 371 (c)(1),
(2), (4) Date: Jul. 3, 2001

(87) PCT Pub. No.: WO00/40535

PCT Pub. Date: Jul. 13, 2000

(30) Foreign Application Priority Data

Jan. 8, 1999 (FR) ............................................ 99 00171

(51) Int. Cl.[7] .............................................. C07C 41/09
(52) U.S. Cl. ....................... 568/626; 568/630; 568/633; 568/648
(58) Field of Search ........................ 568/39, 626, 630, 568/633, 648; 546/339, 152; 549/505, 66, 462; 548/491

(56) References Cited

U.S. PATENT DOCUMENTS

| | | | | |
|---|---|---|---|---|
| 5,614,641 A | * | 3/1997 | Genet et al. ................. | 549/313 |
| 5,648,548 A | * | 7/1997 | Takaya et al. ................. | 568/17 |
| 6,194,616 B1 | * | 2/2001 | Spagnol et al. ............. | 568/322 |
| 6,362,378 B1 | * | 3/2002 | Jacquot et al. .............. | 568/644 |

FOREIGN PATENT DOCUMENTS

| | | | |
|---|---|---|---|
| DE | 44 34 823 | 4/1996 | ......... C07C/43/178 |
| WO | WO 97/48665 | 12/1997 | ........... C07B/41/06 |
| WO | WO 98/22416 | 5/1998 | ........... C07C/41/09 |
| WO | WO 99/02475 | 1/1999 | ........... C07C/41/09 |
| WO | WO 99/06343 | 2/1999 | ........... C07C/41/26 |

OTHER PUBLICATIONS

XP–002056679 M.J. Climent: "Hydride transfer reactions of benzylic alcohols catalyzed by acid faujasites" Recueil Des Travaux Chimiques Des Pays–Bas, vol. 110, No. 6, Jun. 1991, pp. 275–278.
International Search Report.

* cited by examiner

Primary Examiner—Rosalynd Keys

(57) ABSTRACT

The invention concerns a method for preparing a benzylic-type ether from an aromatic compound. The inventive method for preparing a benzylic-type ether from an aromatic compound is characterised in that it consists in: in a first step, acylating an aromatic compound by reacting said aromatic compound with an acylating agent, in the presence of an efficient amount of zeolite or a Friedel-Crafts catalyst leading to a ketonic compound; in a second step, reducing the carbonyl group into carbinol leading to a benzylic alcohol; in a third step, etherifying the hydroxyl group, by reacting the benzylic alcohol with another alcohol, in the presence of an efficient amount of zeolite.

86 Claims, No Drawings

METHOD FOR PREPARING A BENZYLIC-TYPE ETHER

This application is an application under 35 U.S.C. Section 371 of International Application Number PCT/FR00/00024 filed on Jan. 07, 2000.

The present invention relates to a process for preparing a benzyl type ether from an aromatic compound.

The term "benzyl type ether" means a compound comprising at least one aromatic carbocycle or heterocycle wherein one hydrogen directly bonded to the aromatic ring is replaced by an ether finction.

Benzyl type ethers are not easy to produce on an industrial scale.

Not only are the reactants generally expensive, but also secondary reactions are possible since the starting alcohols and the ethers obtained readily form peroxides, which carry a large risk of explosion.

The aim of the present invention is to provide a process for producing a benzyl type ether from an aromatic compound that can avoid the disadvantages mentioned above.

More precisely, the invention provides a process for preparing a benzyl type ether from an aromatic compound, characterized in that it consists of;
  in a first step, acylating an aromatic compound by reacting said compound with an acylation agent in the presence of an effective quantity of a zeolite or a Friedel-Crafts catalyst to produce a ketone compound;
  in a second step, reducing the carbonyl group to a carbinol group to produce a benzyl type alcohol;
  in a third step, etherifying the hydroxyl group by reacting the benzyl type alcohol with a further alcohol in the presence of an effective quantity of a zeolite.

In accordance with the process of the invention, in the first step, an aromatic compound is acylated by reacting it with an acylation agent.

The term "aromatic compound" as used in the present invention defines the conventional notion of aromaticity as defined in the literature, in particular by Jerry MARCH, "Advanced Organic Chemistry", 4$^{th}$ edition, John Wiley & Sons, 1992, pp. 40 ff.

The term "acylation agent" is used in a generic manner and designates any agent that can enable a carbonyl group to be attached to an aromatic nucleus, in particular benzoylation agents.

More precisely, the present invention provides a process for acylating an aromatic compound with general formula (I):

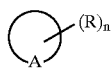

in which:
  A represents the residue of a cycle forming all or a portion of an aromatic, monocyclic or polycyclic, carbocyclic or heterocyclic system: said cyclic residue may carry a group R representing a hydrogen atom or one or more identical or different substituents;
  n represents the number of substituents on the cycle.

The invention is of particular application to aromatic compounds with formula (I) in which A is a residue of a cyclic compound preferably containing at least 4 atoms in the cycle, preferably 5 or 6, which may be substituted, and representing at least one of the following cycles:
  an aromatic, monocyclic or polycyclic carbocycle;
  an aromatic, monocyclic or polycyclic heterocycle containing at least one of the heteroatoms O, N or S.

Without in any way limiting the scope of the invention, residue A, which may be substituted, represents the following residue:
  1. of a monocyclic or polycyclic, aromatic carbocyclic compound. The term "polycyclic carbocyclic compound" means:
    a compound constituted by at least two aromatic carbocycles forming ortho- or ortho- and peri-condensed systems between them;
    a compound constituted by at least two carbocycles only one of which is aromatic and forming-ortho- or ortho- and peri-condensed systems between them.
  2. of an aromatic, monocyclic or polycyclic heterocyclic compound. The term "polycyclic heterocyclic compound" means:
    a compound constituted by at least 2 heterocycles containing at least one heteroatom in each cycle wherein at least one of the two cycles is aromatic and between them they form ortho- or ortho- and peri-condensed systems;
    a compound constituted by at least one hydrocarbon cycle and at least one heterocycle wherein at least one of the cycles is aromatic and between them they form ortho- or ortho- and peri-condensed systems.
  3. of a compound constituted by a concatenation of cycles, as defined in paragraphs 1 and/or 2 bonded together:
    by a covalent bond;
    by an alkylene or alkylidene group containing 1 to 4 carbon atoms, preferably a methylene or isopropylidene group;
    by one of the following groups:

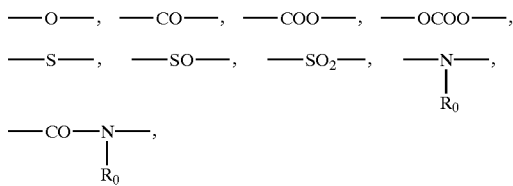

in which formulae, $R_0$ represents a hydrogen atom or an alkyl group containing 1 to 4 carbon atoms, a cyclohexyl group or a phenyl group.

More particularly, residue A, which may be substituted, represents the residue:
  of an aromatic monocyclic carbocyclic compound such as benzene, toluene, isobutylbenzene, anisole, thioanisole, phenetole or veratrole, guaiacol, guetol;
  of an aromatic condensed polycyclic compound such as naphthalene or 2-methoxynaphthalene;
  of an aromatic, carbocyclic, non condensed polycyclic compound such as phenoxybenzene;
  of a partially aromatic, carbocyclic condensed polycyclic compound such as tetrahydronaphthalene or 1,2-methylenedioxybenzene;
  of a partially aromatic, carbocyclic non condensed polycyclic compound such as cyclohexylbenzene;
  of an aromatic, heterocyclic, monocyclic compound such as pyridine, furan or thiophene;
  of an aromatic, partially heterocyclic, condensed polycyclic compound such as quinoline, indole or benzofuran;

of an aromatic, partially heterocyclic, non condensed polycyclic compound such as phenylpyridines or naphthylpyridines;

of a partially aromatic, partially heterocyclic condensed polycyclic compound such as tetrahydroquinoline;

of a partially aromatic, partially heterocyclic non condensed polycyclic compound such as cyclohexylpyridine.

In the process of the invention, an aromatic compound with formula (I) is preferably used in which A represents an aromatic nucleus, preferably a benzene or naphthalene nucleus.

The aromatic compound with formula (I) may carry one or more substituents.

The number of substituents present on the cycle depends on the carbon condensation of the cycle and the presence or otherwise of unsaturated bonds on the cycle.

The maximum number of substituents that can be carried by a cycle can readily be determined by the skilled person.

In the present text, the term "plurality" generally means less than five substituents on an aromatic nucleus.

Examples of substituents are given below but this list is not limiting in nature. Particular examples that can be cited are:

linear or branched alkyl groups, preferably containing 1 to 6 carbon atoms, more preferably 1 to 4 carbon atoms;

linear or branched alkenyl groups, preferably containing 2 to 6 carbon atoms, more preferably 2 to 4 carbon atoms;

linear or branched halogenoalkyl groups, preferably containing 1 to 6 carbon atoms and 1to 13 halogen atoms, more preferably 1 to 4 carbon atoms and 1 to 9 halogen atoms;

cycloalkyl groups containing 3 to 6 carbon atoms, preferably cyclohexyl;

the phenyl group;

the benzyl group;

the hydroxyl group;

the $NO_2$ group;

$R_1$—O— alkoxy groups or $R_1$—S— thioether groups in which $R_1$ represents a linear or branched alkyl group containing 1 to 6 carbon atoms, preferably 1 to 4 carbon atoms, or the phenoxy group; and alkenyloxy groups, preferably an allyloxy group;

—N—$(R_2)_2$ groups, in which groups $R_2$, which may be identical or different, represent a hydrogen atom, a linear or branched alkyl group containing 1 to 6 carbon atoms, more preferably 1 to 4 carbon atoms, or a phenyl group;

—NH—CO—$R_2$ groups, where group $R_2$ has the meaning defined above;

carboxy groups or $R_2$—O—CO— derivatives in which group $R_2$ has the meaning defined above;

acyloxy or aroyloxy $R_1$—CO—O— groups in which group $R_1$ has the meaning defined above;

a halogen atom, preferably a fluorine atom;

a $CF_3$ group;

two groups R placed on two neighbouring carbon atoms may together with the carbon atoms carrying them form a cycle containing 5 to 7 atoms, optionally comprising a further heteroatom.

When n is 2 or more, two groups R and two successive atoms of the aromatic cycle can be bonded together by an alkylene, alkenylene or alkenylidene group containing 2 to 4 carbon atoms to form a saturated, unsaturated or aromatic heterocycle containing 5 to 7 carbon atoms. One or more carbon atoms can be replaced by a further heteroatom, preferably oxygen or sulphur. Groups R may represent a methylenedioxy or ethylenedioxy group or a methylenedithio or ethylenedithio group.

More particularly, the present invention is applicable to aromatic compounds with formula (I) where group or groups R represent an electron-donating group.

The term "electron-donating group" means a group as defined by H. C. BROWN in the work by Jerry MARCH—"Advanced Organic Chemistry", Chapter 9, pages 243 and 244 (1985).

The aromatic compounds used preferably have formula (Ia):

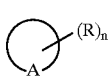

(Ia)

in which:

A represents the residue of a cycle forming all or a portion of a monocyclic or polycyclic aromatic carbocyclic or heterocyclic system: said cyclic residue may carry a group R representing a hydrogen atom or one or more electron-donating substituents, which may be identical or different;

n represents the number of substituents on the cycle.

Examples of preferred electron-donating groups R that can be cited are:

a linear or branched alkyl group containing 1 to 6 carbon atoms, preferably 1 to 4 carbon atoms, such as methyl, ethyl, propyl, isopropyl, butyl, isobutyl, sec-butyl or tert-butyl;

a linear or branched alkenyl group containing 2 to 6 carbon atoms, preferably 2 to 4 carbon atoms, such as vinyl or allyl;

a cyclohexyl, phenyl or benzyl group;

a linear or branched alkoxy group containing 1 to 6 carbon atoms, preferably 1 to 4 carbon atoms, such as methoxy, ethoxy, propoxy, isopropoxy, butoxy or an alkenyloxy group, preferably an allyloxy group, or a phenoxy group;

a hydroxyl group;

a substituted amino group —N—$(R_2)_2$ in which $R_2$ has the meaning defined above;

two groups R may be bonded together to form alkylenedioxy or alkylenedithio groups, preferably a methylenedioxy, ethylenedioxy, methylenedithio or ethylenedithio group.

In formula (Ia), n is a number equal to 4 or less, preferably 1 or 2.

As mentioned above, the process of the invention is particularly applicable for acylating aromatic ethers and thioethers.

Preferred formulae for said compounds are as follows:

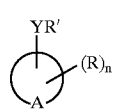

(I')

in which:

Y represents an oxygen atom or a sulphur atom;

A represents the residue of a cycle forming all or a portion of a monocyclic or polycyclic, aromatic carbocyclic system comprising at least one YR' group; said cyclic residue may carry one or more substituents;

R represents one or more substituents which may be identical or different;

R' represents a hydrocarbon group containing 1 to 24 carbon atoms, which may be a linear or branched, saturated or unsaturated acyclic aliphatic group; a saturated, unsaturated or aromatic, monocyclic or polycyclic cycloaliphatic group; or a linear or branched, saturated or unsaturated aliphatic group carrying a cyclic substituent;

R' and R can form a cycle optionally containing a further heteroatom;

n is a number equal to 4 or less.

In the present text, for simplification, the terms "alkoxy or thioether groups" respectively mean groups of the type R'—O— or R'—S—in which R' has the meaning defined above. Thus R' represents both a saturated, unsaturated or aromatic, aliphatic, acyclic or cycloaliphatic group and a saturated or unsaturated aliphatic group carrying a cyclic substituent.

The aromatic ether or thioether involved in the process of the invention has formula (I') in which R' represents a linear or branched, saturated or unsaturated acyclic aliphatic group.

More preferably, R' represents a linear or branched alkyl group containing 1 to 12 carbon atoms, preferably 1 to 6 carbon atoms: the hydrocarbon chain can optionally be interrupted by a heteroatom (for example oxygen), by a functional group (for example —CO—) and/or may carry substituents (for example, one or more halogen atoms).

The linear or branched, saturated or unsaturated acyclic aliphatic group can optionally carry a cyclic substituent. The term "cycle" preferably means a saturated, unsaturated or aromatic carbocyclic cycle, preferably cycloaliphatic or aromatic, in particular cycloaliphatic containing 6 carbon atoms in the cycle, or benzenic.

The acyclic aliphatic group may be bonded to the cycle by a covalent bond, a heteroatom or a functional group; examples will be given below.

The cycle can optionally be substituted; examples of cyclic substituents that can be envisaged include substituents such as R, the meanings of which were given above for formula (I').

R' can also represent a carbocyclic group that is saturated or contains 1 or 2 unsaturated bonds in the cycle, generally containing 3 to 8 carbon atoms, preferably 6 carbon atoms in the cycle; said cycle can be substituted by substituents such as R.

R' can also represent an aromatic carbocyclic group, preferably monocyclic, generally containing at least 4 carbon atoms, preferably 6 carbon atoms in the cycle; said cycle can be substituted by substituents such as R.

In general formula (I') for aromatic ethers or thioethers, residue A can represent the residue of an aromatic monocyclic carbocyclic compound containing at least 4 carbon atoms, preferably 6 carbon atoms, or the residue of a polycyclic carbocycle compound that can be constituted by at least 2 aromatic carbocycles and form ortho- or ortho- and peri-condensed systems between them, or by at least 2 carbocycles at least one of which is aromatic and forms ortho- or ortho- and peri-condensed systems between them. More particularly, a naphthalene residue can be cited.

Residue A can carry one or more substituents on the aromatic nucleus.

Reference can be made to the examples of substituents given for formula (I), but this list is in no way limiting in nature. Any substituent can be present on the cycle provided that it does not interfere with the desired product.

Residue A can, inter alia, carry more than one alkoxy group. In accordance with the process of the invention, it is possible to acylate polyalkoxylated compounds.

More preferably, in formula (I'), R represents one of the following groups:

a linear or branched alkyl group containing 1 to 6 carbon atoms, preferably 1 to 4 carbon atoms, such as methyl, ethyl, propyl, isopropyl, butyl, isobutyl, sec-butyl, tert-butyl;

a linear or branched alkoxy group containing 1 to 6 carbon atoms, preferably 1 to 4 carbon atoms, such as methoxy, ethoxy, propoxy, isopropoxy, butoxy, isobutoxy, sec-butoxy, tert-butoxy;

a halogen atom, preferably a fluorine, chlorine or bromine atom, or a trifluoromethyl group.

More particularly, the process of the invention is applicable to aromatic ethers or thioethers with formula (I'a):

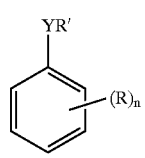

(I'a)

in which:

n is a number equal to 4 or less, preferably 0 or 1;

Y represents an oxygen atom or sulphur;

group R' represents a linear or branched alkyl group containing 1 to 6 carbon atoms, preferably 1 to 4 carbon atoms, such as methyl, ethyl, propyl, isopropyl, butyl, isobutyl, sec-butyl, tert-butyl, or a phenyl group;

group or groups R, which may be identical or different, represent one of the following groups:

a hydrogen atom;

a linear or branched alkyl group, preferably containing 1 to 6 carbon atoms, more preferably 1 to 4 carbon atoms;

a linear or branched alkenyl group, preferably containing 2 to 6 carbon atoms, more preferably 2 to 4 carbon atoms;

a linear or branched halogenoalkyl group, preferably containing 1 to 6 carbon atoms and 1 to 13 halogen atoms, more preferably 1 to 4 carbon atoms and 1 to 9 halogen atoms;

a cycloalkyl group containing 3 to 6 carbon atoms, preferably a cyclohexyl group;

a phenyl group;

a benzyl group;

a hydroxyl group;

a $NO_2$ group;

an $R_1$—O— alkoxy group or an $R_1$—S— thioether group in which $R_1$ represents a linear or branched alkyl group containing 1 to 6 carbon atoms, more preferably 1 to 4 carbon atoms, or a phenyl group; or an alkenyloxy group, preferably an allyloxy group;

a —N—$(R_2)_2$ group where groups $R_2$, which may be identical or different, represent a hydrogen atom, a linear or branched alkyl group containing 1 to 6 carbon atoms, more preferably 1 to 4 carbon atoms, or a phenyl group;

a —NH—CO—R₂ group, where group R₂ has the meaning defined above; a carboxy group or a R₂—O—CO— derivative in which R₂ has the meaning defined above;

an acyloxy or aroyloxy group R₁—CO—O— in which group R₁ has the meaning defined above;

a halogen atom, preferably a fluorine atom;

a CF₃ group;

groups R' and R placed on two neighbouring carbon atoms can together with the carbon atoms carrying them form a cycle containing 5 to 7 atoms, optionally containing a further heteroatom.

When n is 1 or more, groups R' and R and the two successive atoms on the benzene ring can be bonded together and form an alkylene, alkenylene or alkenylidene group containing 2 to 4 carbon atoms to form a saturated, unsaturated or aromatic heterocycle containing 5 to 7 atoms. One or more carbon atoms can be replaced by a further heteroatom, preferably oxygen or sulphur. Groups OR' and R can represent a methylenedioxy or ethylenedioxy group and groups SR' and R can represent a methylenedithio or ethylenedithio group.

In formula (I'a), R' preferably represents a linear or branched alkyl group containing 1 to 6 carbon atoms, preferably a methyl or ethyl group or a phenyl group.

The benzene nucleus carries one or more substituents R, which may be identical or different. R preferably represents a linear or branched alkyl group containing 1 to 6 carbon atoms, preferably a methyl or ethyl group; or a linear or branched alkoxy group containing 1 to 4 carbon atoms, preferably a methoxy or ethoxy group.

More particularly, the process of the invention is applicable to aromatic ethers or thioethers with formula (I') or (I'a) in which:

n is 0 or 1;

R' represents a linear or branched alkyl group containing 1 to 6 carbon atoms or a phenyl group, preferably a methyl or ethyl group;

R represents a linear or branched alkyl group containing 1 to 6 carbon atoms, preferably a methyl or ethyl group; or a linear or branched alkoxy group containing 1 to 4 carbon atoms, preferably a methoxy or ethoxy group;

Groups YR' and R form a methylenedioxy, ethylenedioxy, methylenedithio or ethylenedithio group.

Illustrative examples of compounds with formula (I) or (I') that can in particular be mentioned are:

aromatic compounds such as benzene, toluene, fluorobenzene, chlorotoluenes, fluorotoluenes, trifluoromethoxybenzene, trichloromethoxytoluene, trifluoromethylthiobenzene;

aminated aromatic compounds such as aniline;

phenolic compounds such as phenol, o-cresol, guaiacol, guetol, α-naphthol, β-naphthol;

monoethers such as anisole, ethoxybenzene (phenetole), propoxybenzene, isopropoxybenzene, butoxybenzene, isobutoxybenzene, 1-methoxynaphthalene, 2-ethoxynaphthalene; substituted monoethers such as 2-chloroanisole, 3-chloroanisole, 2-bromoanisole, 3-bromoanisole, 2-methylanisole, 3-methylanisole, 2-ethylanisole, 3-ethylanisole, 2-isopropaylanisole, 3-isopropylanisole, 2-propylanisole, 3-propylanisole, 2-allylanisole, 2-butylanisole, 3-butylanisole, 2-benzylanisole, 2-cyclohexylanisole, 1-bromo-2-ethoxybenzene, 1-bromo-3-ethoxybenzene, 1-chloro-2-ethoxybenzene, 1-chloro-3-ethoxybenzene, 1-ethoxy-2-ethylbenzene, 1-ethoxy-3-ethylbenzene, 1-methoxy-2-allyloxybenzene, 2,3-dimethylanisole, 2,5-dimethylanisole;

diethers such as veratrole, 1,3-dimethoxybenzene, 1,4-dimethoxybenzenes, 1,2-diethoxybenzene, 1,3-diethoxybenzene, 1,2-dipropoxybenzene, 1,3-dipropoxybenzene, 1,2-methylenedioxybenzene, 1,2-ethylenedioxybenzene;

triethers such as 1,2,3-trimethoxybenzene, 1,3,5-trimethoxybenzene, 1,3,5-triethoxybenzene;

thioethers such as thioanisole, o-thiocresol, m-thiocresol, p-thiocresol, 2-thioethylnaphthalene, S-phenylthioacetate, 3-(methylmercapto)aniline, phenylthiopropionate.

Compounds for which the process of the invention is of particular interest are benzene, toluene, isobutylbenzene, anisole, phenetole, veratrole, 1,2-methylenedioxybenzene, 2-methoxynaphthalene and thioanisole.

Regarding the acylation reactant, it is possible to use carboxylic acids and their derivatives, halides or anhydrides, preferably anhydrides.

More particularly, the acylation reactant has formula (II):

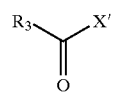

(II)

in which:

R₃ represents:
a linear or branched, saturated or unsaturated aliphatic group containing 1 to 24 carbon atoms; a monocyclic or polycyclic, saturated, unsaturated or aromatic cycloaliphatic group containing 3 to 8 carbon atoms; or a linear or branched, saturated or unsaturated aliphatic group carrying a cyclic substituent;

X' represents:
a halogen atom, preferably a chorine or bromine atom;
a hydroxyl group;
a —O—CO—R₄ group, in which R₄, which may be identical to or different from R₃, has the same meaning as R₃; or R₃ and R₄ may together form a divalent linear or branched, saturated or unsaturated aliphatic group containing at least 2 carbon atoms.

The term "cyclic substituent" has been defined above.

More preferably, R₃ represents a linear or branched alkyl group containing 1 to 12 carbon atoms, preferably 1 to 6 carbon atoms: the hydrocarbon chain can optionally be interrupted by a heteroatom (for example oxygen), by a functional group (for example —CO—) and/or can carry a substituent (for example a halogen or a CF₃ group).

R₃ preferably represents an alkyl group containing 1 to 4 carbon atoms, such as methyl, ethyl, propyl, isopropyl, butyl, isobutyl, sec-butyl or tert-butyl, or a cycloalkyl group containing 3 to 8 carbon atoms, preferably a cyclopentyl or cyclohexyl group.

R₃ also represents an alkenyl group containing 2 to 10 carbon atoms, in particular a vinyl, propen-yl, buten-yl, penten-yl, hexen-yl, octen-yl or decen-yl group.

Group R₃ also preferably represents a phenyl group that can optionally be substituted. Any substituent can be present on the cycle provided that it does not interfere with the desired product.

R₃ also represents a phenylalkyl group containing 7 to 12 carbon atoms, preferably a benzyl group.

More particular examples of substituents that can be cited are:

a linear or branched alkyl group containing 1 to 6 carbon atoms, preferably 1 to 4 carbon atoms, such as methyl, ethyl, propyl, isopropyl, butyl, isobutyl, sec-butyl or tert-butyl;

a linear or branched alkoxy group containing 1 to 6 carbon atoms, preferably 1 to 4 carbon atoms, such as a methoxy, ethoxy, propoxy, isopropoxy, butoxy, isobutoxy, sec-butoxy or tert-butoxy group;

a hydroxyl group;

a halogen atom, preferably a fluorine, chlorine or bromine atom.

Preferred acylation agents are acid anhydrides. More particularly, they have formula (II) in which $R_3$ and $R_4$ are identical and represent an alkyl group containing 1 to 4 carbon atoms, or a phenyl group.

When the acylation agent is an acid halide, it preferably has formula (II) where X' represents a chlorine atom and $R_3$ represents a methyl, ethyl or phenyl group.

Particular illustrative examples of acylation agents with formula (II) that can be cited are:

acetic anhydride;
propanoic anhydride;
butyric anhydride;
isobutyric anhydride;
trifluoroacetic anhydride;
benzoic anhydride;
monochloroacetyl anhydride;
dichloroacetyl anhydride;
acetyl chloride;
monochloroacetyl chloride;
dichloroacetyl chloride;
propanoyl chloride;
isobutanoyl chloride;
pivaloyl chloride;
stearoyl chloride;
crotonyl chloride;
benzoyl chloride;
chlorobenzoyl chlorides;
p-nitrobenzoyl chloride;
methoxybenzoyl chloride;
naphthoyl chloride;
acetic acid;
benzoic acid.

Acetic anhydride, propanoic anhydride, benzoic anhydride, monochloroacetyl anhydride, dichloroacetyl anhydride and benzoyl chlorides are preferred acylation agents.

In accordance with the process of the invention, in a first step, the aromatic compound with formula (I), preferably (I'), (Ia) and more preferably (I'a) is acylated using a compound with formula (II) in the presence of a catalyst.

In a first variation of the process of the invention, t he aromatic compound with formula (I) is acylated in the presence of a zeolitic catalyst.

The term "zeolite" means a crystalline tectosilicate of natural or synthetic origin the crystals of which result from a three dimensional assembly of tetrahedral $SiO_4$ and $TO_4$ units: T represents a trivalent element such as aluminium, gallium or iron, preferably aluminium.

Aluminosilicate type zeolites are the best known.

Within the crystalline matrix, zeolites have a system of cavities interconnected by channels with a well defined diameter known as pores.

The zeolites can have a unidimensional, bidimensional or three-dimensional channel matrix.

A natural or synthetic zeolite can be used in the process of the invention.

Examples of natural zeolites that can be cited are: chabazite, clinoptilolite, erionite, phillipsite and offretite.

Synthetic zeolites are also suitable for use in the invention.

Examples of unidimensional synthetic zeolites that can be cited include ZSM-4, L zeolite, ZSM-12 zeolite, ZSM-22 zeolite, ZSM-23 zeolite and ZSM-48 zeolite.

Examples of two-dimensional zeolites that can be used include mordenite and ferrierite.

Particular examples of three-dimensional zeolites that can be mentioned are: β zeolite, Y zeolite, X zeolite, ZSM-5 zeolite, ZSM-11 zeolite and offretite.

Preferably, synthetic zeolites are used, in particular zeolites with the following forms:

mazzite with a Si/Al mole ratio of 3.4;

L zeolite with a Si/Al mole ratio of 1.5 to 3.5;

mordenite with a Si/Al mole ratio of 5 to 100, preferably 5 to 50;

ferrierite with a Si/Al mole ratio of 3 to 10;

offretite with a Si/Al mole ratio of 4 to 8.5;

β zeolites with a Si/Al mole ratio of more than 8, preferably in the range 10 to 100, more preferably in the range 12 to 50;

Y zeolites, in particular zeolites obtained after dealumination treatment (for example hydrotreatment, washing with hydrochloric acid or treatment with $SiCl_4$), more particularly US-Y zeolites with a Si/Al mole ratio of more than 2, preferably in the range 4to60;

Faujasite type X zeolite with a Si/Al mole ratio of 0.7 to 1.5;

ZSM-5 zeolites or aluminium silicalite with a Si/Al mole ratio of 10 to 500;

ZSM-11 zeolite with a Si/Al mole ratio of 5 to 30;

Mesoporous MCM type zeolite, more particular MCM-22 and MCM-41 with a Si/Al mole ratio in the range 10 to 100, preferably in the range 15 to 40.

The zeolites are advantageously used in the acid form.

Of the zeolites, mordenite, β or Y zeolites in the acid form are preferably used in the process of the invention.

The zeolites used in the process of the invention are known products described in the literature (see "Atlas of Zeolite Structure Types" by W. M. Meier and D. H. Olson, published by the Structure Commission of the International Zeolite Association (1978)).

Commercially available zeolites or zeolites synthesised using the processes described in the literature can be used.

Reference in this respect should be made to the above Atlas, more particularly for the preparation:

of L zeolite, to the publication by Barrer R. M. et al., Z. Kristallogr., 128, pp. 352 (1969);

of ZSM-12 zeolite, to U.S. Pat. No. 3,832,449 and the article by La Pierre et al., Zeolites 5, pp. 346 (1985);

of ZSM-22 zeolite, to the publication by Kokotailo G. T. et al., Zeolites 5, pp. 349 (1985);

of ZSM-23 zeolite, to U.S. Pat. No. 4,076,842 and the article by Rohrman A. C. et al., Zeolites 5, pp. 352 (1985);

of ZSM-48 zeolite, to the work by Schenkler J. L. et al., Zeolites 5, pp. 355 (1985);

of β zeolite, to U.S. Pat. No. 3,308,069 and the article by Caullet P. et al., Zeolites 12, pp. 240 (1992);

of mordenite, to the work by Itabashi et al., Zeolites 6, pp. 30 (1986);

of X and Y,zeolites, respectively to U.S. Pat. No. 2,882,244 and U.S. Pat. No. 3,130,007;

of ZSM-5 zeolite, to U.S. Pat. No. 3,702,836 and to the article by Shiralkar V. P. et al., Zeolites 9, pp. 363 (1989);

of ZSM-11 zeolite, to the work by Harrison I. D. et al., Zeolites 7, pp. 21 (1987);

of mesoporous MCM type zeolite, to the article by Beck et al., J. Am. Chem. Soc., 114, (27), pp. 10834–43 (1992).

The zeolite constitutes the catalytic phase. It can be used alone or mixed with a mineral matrix. In the description, the term "catalyst" means the catalyst formed entirely from zeolite or mixed with a matrix prepared using techniques that are known to the skilled person.

To this end, the matrix can be selected from oxides of metals such as aluminium, silicon and/or zirconium oxides, or from clays, more particularly kaolin, talc or montmorillonite.

In the catalyst, the amount of active phase represents 5% to 100% by weight of the catalyst.

The catalysts can be in different forms in the process of the invention: powder, formed products such as granules (for example extrudates or beads) or pellets, which are obtained by extrusion, moulding, compacting or any other known process. In practice, on an industrial scale, granules or beads are the most advantageous both as regards effectiveness and as regards ease of processing.

In accordance with the invention, the acylation reaction is advantageously carried out in the liquid phase comprising the aromatic compound and the acylation agent in the presence of a catalyst.

One of the starting reactants can act as a reaction solvent but it is also possible to use an organic solvent.

An organic solvent is selected that is less activated than the starting substrate and which preferably dissolves the latter.

Examples of suitable solvents that can in particular be cited are aliphatic or aromatic hydrocarbons, which may or may not be halogenated, and aliphatic, cycloaliphatic or aromatic ether-oxides.

Particular examples of aliphatic hydrocarbons that can be cited are paraffins such as hexane and cyclohexane, aromatic hydrocarbons, in particular aromatic hydrocarbons such as benzene, toluene, xylenes, cumene, and petroleum cuts constituted by a mixture of alkylbenzenes, in particular Solvesso® type cuts.

Particular examples of aliphatic or aromatic halogenated hydrocarbons that can be mentioned are: perchlorinated hydrocarbons such as tetrachloroethylene or hexachloroethane; and partially chlorinated hydrocarbons such as 1,2-dichloroethane or dichlorobenzene.

It is also possible to use organic solvents such as aliphatic, cycloaliphatic or aromatic ether-oxides, more particularly dipropyl oxide, diisopropyl oxide, dibutyl oxide, methyltertiobutylether, ethylene glycol dimethylether (glyme), di-ethylene glycol dimethylether (diglyme); phenyl oxide; dioxane, tetrahydrofuran (THF).

Examples of more polar aprotic organic solvents that can be used in the process of the invention that can be cited are nitrated compounds such as nitromethane, nitroethane, 1-nitropropane, 2-nitropropane or mixtures thereof, nitrobenzene; aliphatic or aromatic nitriles such as acetonitrile, propionitrile, benzonitrile, benzyl cyanide; linear or cyclic carboxamides such as N,N-dimethylacetamide (DMAC), N,N-diethylacetamide, dimethylformamide (DMF), diethylformamide or 1-methyl-2-pyrrolidinone (NMP); dimethylsulphoxide (DMSO); tetramethylensulphone (sulpholane); hexamethyl-phosphotriamide (HMPT).

Preferred solvents are: dichloromethane, dichlorobenzene, ethylene glycol dimethylether (glyme), di-ethylene glycol dimethylether (diglyme) and dioxane.

It is also possible to use a mixture of organic solvents.

Preferably, the starting substrate is used as the reaction solvent.

As mentioned above, the aromatic compound is reacted with an acylation agent, optionally in the presence of a reaction solvent as defined and in the presence of a zeolitic catalyst.

The ratio between the number of moles of aromatic compound and the number of moles of acylation agent can vary as the substrate can act as the reaction solvent. The ratio can be from 0.1 to 10, and is preferably in the range 0.5 to 4.0.

The quantity of catalyst used in the process of the invention can vary within wide limits.

When the process is a batch process, the catalyst can represent 0.01% to 50%, preferably 5% to 25% by weight of the aromatic compound employed. However, if the process is carried out continuously, for example by reacting a mixture of the aromatic compound and the acylation agent on a fixed catalyst bed, these catalyst/aromatic compound ratios have no meaning at a given moment, there may be an excess of catalyst with respect to the weight of aromatic starting compound.

The quantity of organic solvent employed is generally selected such that the ratio between the number of moles of organic solvent and the number of moles of aromatic compound is preferably in the range 0 to 100, more preferably in the range 0 to 50.

The temperature at which the acylation reaction is carried out depends on the reactivity of the starting substrate and that of the acylation agent.

It is in the range 20° C. to 300° C., preferably in the range 40° C. to 150° C.

In general, the reaction is carried out at atmospheric pressure, but lower or higher pressures can also be used. Autogenous pressure is applied when the reaction temperature is higher than the boiling point of the reactants and/or products.

From a practical viewpoint, the process can be carried out batchwise or continuously.

In the first variation, there are no constraints as regards how the reactants are used. They can be introduced in any order.

After bringing the reactants into contact, the reaction mixture is heated to the desired temperature.

In the other variation, the reaction is carried out continuously in a tube reactor comprising the solid catalyst disposed in a fixed bed.

The aromatic compound and acylation agent can be introduced into the reactor separately or as a mixture.

Said mixture is passed over a catalytic bed comprising at least one zeolite then the reaction mixture from the catalytic bed is re-circulated over the catalytic bed for the number of times required to obtain the desired degree of substrate conversion.

Acylation of an aromatic compound on a zeolite catalytic bed with re-circulation of the reaction mixture is a technique that has been described in PCT/FR97/01066, publication number WO-A-97/48665, which is hereby incorporated by reference.

The reaction mixture traverses the catalytic bed, preferably from bottom to top and at its outlet, it is returned to the reactant mixing zone to be recycled for the number of times required to obtain the desired substrate degree of conversion, preferably more than 20%, more preferably in the range 50% to 100%. The substrate degree of conversion is defined as the ratio of the number of moles of substrate transformed to the number of moles of substrate introduced.

The linear velocity of the liquid flux over the catalytic bed is advantageously in the range 0.1 to 10 cm/s, preferably in the range 0.1 to 5 cm/s.

The residence time for the material flux on the catalytic bed is, for example, in the range 15 min to 10 h, preferably in the range 30 min to 5 h.

At the end of the reaction, a liquid phase is recovered comprising the aromatic ketone compound which can be recovered conventionally, by distillation or by re-crystallisation from a suitable solvent, for example water or alcohols (methanol, ethanol), after prior elimination of the excess reactants.

More particularly, the product obtained has the following formula (III):

(III)

in which R, $R_3$, A and n have the meanings defined above.

Preferably, the process of the invention can produce the compound with formula (III'):

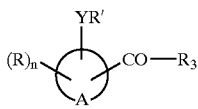
(III')

in which R, R', $R_3$, Y, A and n have the meanings defined above.

Preferably, the compounds obtained have formula (IIIa):

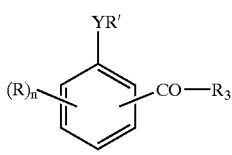
(IIIa)

in which R, R', $R_3$, Y and n have the meanings defined above.

In a further variation, the invention consists of using homogeneous catalysis, employing organic or mineral type Friedel-Crafts catalysts.

Examples of salts comprising an organic counter-ion that can be cited include the acetate, propionate, benzoate, methanesulphonate, trifluoromethanesulphonate of metallic or metalloid elements from groups (IIIa), (IVa), (VIII), (IIb), (IIIb), (IVb), (Vb) and (VIb) of the periodic table.

Salts comprising an inorganic counter-ion that can be cited are: chlorides, bromides, iodides, sulphates, phosphates, nitrates, oxides and analogous products of metallic or metalloid elements from groups (IIa), (IIIa), (IVa), (VIII), (IIb), (IIIb), (IVb), (Vb) and (VIb) of the periodic table.

In the present text, reference to the periodic table means that published in the Bulletin de la Société Chimique de France, n° 1 (1966).

More particularly, the salts used in the process of the invention are those of elements from group (IIa) of the periodic table, preferably magnesium; group (IIIa), preferably scandium, yttrium and the lanthanides; group (IVa), preferably titanium, zirconium; group (VIII), preferably iron; group (IIb), preferably zinc; group (IIIb), preferably boron, aluminiun, gallium, indium; group (IVb), preferably tin; group (Vb), preferably bismuth; group (VIb), preferably tellurium.

Inorganic salts that can be cited include metallic halides, preferably magnesium chloride, zirconium chloride, ferric chloride, zinc chloride, aluminium chloride, aluminium bromide, gallium chloride, indium chloride, stannic chloride, bismuth chloride and boron trifluoride.

Regarding the organic salts, rare earth and/or bismuth salts of trifluoromethanesulphonic acid, commonly known as triflic acid, are preferably used.

The term "rare earth" means lanthanides with an atomic number of 57 to 71 and yttrium, as well as scandium.

More particularly, the process of the invention envisages using the following rare earths: lanthanum, ytterbium, lutetium and/or scandium.

Rare earth triflates are known products that have been described in the literature, in particular in U.S. Pat. No. 3,615,169. They are generally obtained by reacting a rare earth oxide and trifluoromethanesulphonic acid.

The salts of bismuth and triflic acid described in PCT patent application PCT/FR96/01488 can also be employed in the process of the invention.

In accordance with the process of the invention, the compound with formula (I) is acylated.

The process of the invention can be carried out in an organic solvent, for example isopropyl ether, but one of the reactants can also be used as the reaction solvent.

Preferably, the solvent is anhydrous.

The ratio between the number of moles of compound with formula (I) and the number of moles of acylation agent (compound with formula (II)) can vary as the substrate may act as the reaction solvent. The ratio can be from 1 to 10, preferably 1 to 4.0.

The quantity of catalyst used is determined such that the ratio between the number of moles of catalyst and the number of moles of compound with formula (II) is preferably in the range 0.001 to 2.0, more preferably in the range 0.05 to 1.0.

The temperature at which the acylation reaction is carried out depends on the reactivity of the starting substrate and that of the acylation agent.

It is in the range 20° C. to 200° C., preferably in the range 40° C. to 120° C.

In general, the reaction is carried out at atmospheric pressure, but lower or higher pressures may also be suitable.

Preferably, the reaction is carried out under a controlled atmosphere of inert gas such as nitrogen or rare gases, for example argon.

From a practical viewpoint, the compound with formula (I), the catalyst and then the compound with formula (II) are processed in that order.

After bringing the reactants into contact, the reaction mixture is heated to the desired temperature.

The reaction period is a function of a number of parameters. It is usually in the range 1 hour to 8 hours.

After acylating the compound with formula (I), an aromatic ketone compound with formula (III), preferably (III') and more preferably (IIIa) is obtained.

It is recovered from the reaction medium conventionally. To this end, a catalyst deactivation treatment is usually carried out first, either by extracting with water or by adding a solution of a basic agent, preferably ammonia or sodium carbonate or bicarbonate, then separating the aqueous and organic phases.

It is then recovered from the organic phase using known techniques, in particular by distillation or re-crystallisation from a suitable solvent, possibly in the presence of water, preferably an alcohol, for example methanol, isopropanol or butanol; or a ketone, for example methylethyl ketone or methylisobutyl ketone.

The acylation step is preferably carried out in the presence of a zeolite type catalyst.

In accordance with the process of the invention, in the second step the carbonyl group is hydrogenated to a carbinol group:

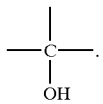

In a first variation of the process of the invention, hydrogenation is carried out in the presence of conventional hydrogenation catalysts.

Preferred catalysts employ metals from group VIII of the periodic table, preferably noble metals, cobalt or nickel.

In the present text, reference to the periodic table means that published in the Bulletin de la Société Chimique de France, n° 1 (1966).

A finely divided noble metal from group VIII of the periodic table can be used such as platinum, palladium, rhodium, iridium, ruthenium or osmium.

Said metal can be supplied in a finely divided form or it can be deposited on a support. Examples of supports that can be mentioned are charcoal, acetylene black, silica, alumina, zirconia, chromium oxide, bentonite, etc.

The metal can be deposited on a support in the metallic form or in the form of a compound that will be reduced to the metal in the presence of hydrogen. This can, inter alia, be an oxide of one of the noble metals cited above.

Preferred metals are platinum and palladium, preferably deposited on carbon black.

Preferably, the platinum and/or palladium is deposited on a support. In general, it is deposited in an amount of 0.5% to 5% by weight of catalyst.

The quantity of hydrogenation catalyst employed, expressed as the weight of catalyst per unit weight of aromatic ketone compound, can be between 0.5% and 20%, preferably between 1% and 5%, for example.

Other hydrogenation catalysts that are also suitable for the process of the invention are Raney nickel and Raney cobalt.

Commercially available forms of Raney nickel can be used that may contain impurities that are routinely found in that type of catalyst, namely chromium and/or iron, but cause no problems.

In that case, the quantity of hydrogenation catalyst used, expressed as the weight of catalyst per unit weight of aromatic ketone compound, can be in the range 1% to 10%, preferably in the range 3% to 6%, for example.

The catalyst can be employed in the form of a powder, pellets or as granules.

The quantity of hydrogenation catalyst used, expressed as the weight of catalyst per mole of aromatic ketone compound, can be in the range 0.5% to 20%, preferably in the range 1% to 5%, for example.

The process of the invention is carried out at a temperature selected from a range of temperatures from 50° C. to 120° C., more particularly 60° C. to 100° C.

The reaction is carried out under hydrogen pressure from a pressure slightly higher than atmospheric pressure to a pressure of several tens of bars. Advantageously, the hydrogen pressure is in the range 1 to 50 bars, more preferably in the range 3 to 10 bars.

The reaction is carried out until hydrogen consumption ceases.

The process of the invention is carried out in the liquid phase.

In a first variation of the process of the invention, the ketone compound is hydrogenated in bulk when the latter and the final product are in the liquid form.

In a further variation of the process of the invention, the reaction is carried out in an organic solvent.

An organic solvent is selected that is less activated than the starting substrate and which preferably dissolves the latter.

A solvent can be used that is inert under the reaction conditions. Saturated cycloaliphatic or aliphatic hydrocarbons can be used such as hexane or cyclohexane, or aromatic hydrocarbons such as benzene, toluene, xylenes; alcohols such as methanol, ethanol, propanol or cyclohexanol; esters such as ethyl acetate or butyl acetate; polyol esters or ethers such as tetraethylene glycol diacetate; or ethers such as ethylene glycol dimethylether (glyme) or diethylene glycol dimethylether (diglyme).

Methanol and ethanol are preferred solvents.

The concentration of ketone compound with formula (III) or (III') or (IIIa) used in the solvent can vary widely up to saturation under the operating conditions. In general, it is not of economic interest to use less than 5% by weight of ketone compound per unit volume of solvent.

In general, the concentration by weight of ketone compound per unit volume of solvent is in the range 20% to 75%, preferably in the range 40% to 60%.

In practice, the process of the invention can be implemented by introducing the ketone compound with formula (III) or (III') or (IIIa), the catalyst and the solvent into an inert autoclave then, after the normal purges, by supplying the autoclave with a suitable pressure of hydrogen; the contents of the autoclave are then heated with stirring to a suitable temperature until absorption ceases. The pressure in the autoclave can be kept constant throughout the reaction by means of a reserve of gas mixture, which is supplied at the selected pressure.

At the end of the reaction, the autoclave is cooled and degassed. The reaction mixture is recovered and the catalyst is separated using conventional solid/liquid separation techniques.

A benzyl type alcohol is obtained, i.e., a compound comprising at least one aromatic heterocycle or carbocycle wherein one hydrogen atom directly bonded to the aromatic nucleus is replaced by the group

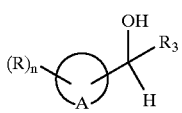
(IV)

The process of the invention produces benzyl type alcohols preferably with formula (IV):

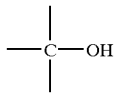

in which R, $R_3$, A and n have the meanings defined above.

The process of the invention preferentially produces a compound with formula (IV'):

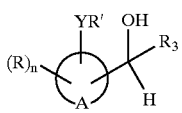
(IV')

in which R, R', $R_3$, Y, A and n have the meanings defined above.

More particularly, preferred compounds of the invention have formula (IVa):

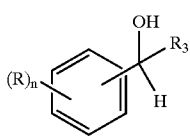
(IVa)

in which R, $R_3$ and n have the meanings defined above.

The reaction medium that is free of the catalyst and comprises the benzyl type alcohol can be directly used in the next step, etherification, if the latter is carried out using methanol or ethanol.

In other cases, the benzyl type alcohol obtained is separated using conventional separation methods, for example distillation or crystallisation, before engaging it in the etherification step.

When the benzyl alcohol obtained with formulae (IV), IV') or (IVa) is a chiral alcohol, a further variation of the process of the invention consists in carrying out enantioselective hydrogenation of the ketone compound, in the presence of a metal complex, preferably based on rhodium, iridium, ruthenium or palladium and comprising an optically active diphosphine type ligand.

The diphosphine can be BINAP or BIPNOR {bis-(1-phospha-2,3-diphenyl-4,5-dimethylnorbomadiene)}.

Hydrogenation of a carbonyl group to a carbinol group in the presence of a metallic complex comprising an optically active diphosphine as mentioned above can be carried out as described in PCT/FR97/01154 published with publication number WO-A-98/00375, which is hereby incorporated into the present application by reference.

In accordance with the process of the invention, in a third step, the hydroxyl group is etherified. This consists of reacting the benzyl type alcohol with a further alcohol in the presence of an effective quantity of a zeolite.

More particularly, the benzyl alcohol obtained has formulae (IV), more preferably formula (IV') and (IVa).

For convenience, the generic term "alkanol" will be used for the other alcohol employed even though it also designates alcohols comprising cycles, in particular aromatic cycles.

Preferred benzyl type alcohols used in the process of the invention are:

vanillic alcohol;
p-hydroxybenzyl alcohol;
1-(4-hydroxy-3-methoxyphenyl)ethanol;
2-hydroxybenzyl alcohol;
3,4-dimethoxybenzyl alcohol;
p-methoxybenzyl alcohol;
6-n-propyl-3,4-dimethoxybenzyl alcohol;
(3,4-dimethoxyphenyl)dimethylcarbinol;
1-(3,4-dimethoxyphenyl)ethanol;
1-[1-hydroxy-2-methylpropyl]-3,4-dimethoxybenzene;
1-[1-hydroxy-2-methylpropyl]-3,4-diethoxybenzene;
1-[1-hydroxyethyl]-3,4-diethoxybenzene;
1-[1-hydroxyethyl]-3,4-dimethoxy-6-propylbenzene;
5-[1-hydroxyethyl]-1,3-benzodioxol;
naphthalene-2-methylol.

More particularly, the alkanol has general formula (V):

$$R_5-OH \qquad (V)$$

in which formula (V):

$R_5$ represents a hydrocarbon containing 1 to 24 carbon atoms, which may be a linear or branched, saturated or unsaturated acyclic aliphatic group; a saturated, unsaturated or aromatic cycloaliphatic group or a linear or branched, saturated or unsaturated aliphatic group carrying a cyclic substituent.

The alkanol used in the process of the invention has formula (V) in which $R_5$ represents a linear or branched, saturated or unsaturated acyclic aliphatic group.

More precisely, $R_5$ represents a linear or branched alkyl, alkenyl, alkadienyl or alkynyl group preferably containing 1 to 24 carbon atoms.

The hydrocarbon chain can optionally be:

interrupted by one of the following groups:

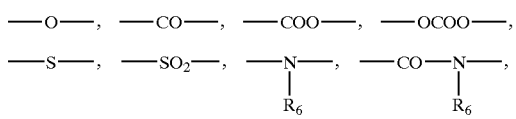

in which $R_6$ represents hydrogen or a linear or branched alkyl group containing 1 to 4 carbon atoms, preferably a methyl or ethyl group;

and/or carries one of the following substituents:
—OH, —OCOO—, —COOR$_6$, —CHO, —NO$_2$, —X, —CF$_3$ in which $R_6$ has the meaning defined above.

The linear or branched, saturated or unsaturated acyclic aliphatic residue can optionally carry a cyclic substituent. The term "cycle" as used here means a saturated, unsaturated or aromatic carbocyclic or heterocyclic cycle.

The acyclic aliphatic residue can be bonded to the cycle by a covalent bond or one of the following groups:

-continued

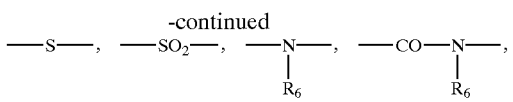

in which $R_6$ has the meaning defined above.

Examples of cyclic substituents that can be envisaged are cycloaliphatic, aromatic or heterocyclic substituents, in particular cycloaliphatic substituents containing 6 carbon atoms in the cycle, or benzenes, these cyclic substituents themselves optionally carrying 1, 2, 3, 4 or 5 groups "R", which may be identical or different, R" having the meaning defined above for group R carried by the cycle with formula (I).

In general formula (V) for alkanols, $R_5$ can also represent a carbocyclic group that is saturated or comprises 1 or 2 unsaturated bonds in the cycle, generally containing 3 to 7 carbon atoms, preferably 6 carbon atoms in the cycle; said cycle can be substituted by 1 to 5 groups R", preferably 1 to 3, R" having the meanings defined above for R.

Preferred examples of groups $R_5$ that can be cited are cyclohexyl or cyclohexen-yl groups, optionally substituted by linear or branched alkyl groups containing 1 to 4 carbon atoms.

The process is readily carried out with the majority of alkanols.

Examples of alkanols that can be cited are:

lower aliphatic alkanols containing 1 to 5 carbon atoms, such as methanol, ethanol, trifluoroethanol, propanol, isopropyl alcohol, butanol, isobutyl alcohol, sec-butyl alcohol, tert-butyl alcohol, pentanol, isopentyl alcohol, sec-pentyl alcohol and tert-pentyl alcohol, ethylene glycol monoethyl ether, methyl lactate, isobutyl lactate, methyl D-lactate, isobutyl D-lactate, propargylic alcohol, 3-chlorobut-2-en-1-ol, 2-butyn-1-ol;

higher aliphatic alcohols containing at least 6 and up to about 20 carbon atoms, such as hexanol, heptanol, isoheptyl alcohol, octanol, isooctyl alcohol, 2-ethylhexanol, sec-octyl alcohol, tert-octyl alcohol, nonanol, isononyl alcohol, decanol, dodecanol, tetradecanol, octadecanol, hexadecanol, oleic alcohol, eicosyl alcohol, diethylene glycol monoethyl ether;

cycloaliphatic alcohols containing 3 to about 20 carbon atoms, such as cyclopropanol, cyclobutanol, cyclopentanol, cyclohexanol, cycloheptanol, cyclooctanol, cyclododecanol, tirpropylcyclohexanol, methylcyclohexanol and methylcycloheptanol, cyclopenten-ol, cyclohexen-ol;

an aliphatic alcohol carrying an aromatic group containing 7 to about 20 carbon atoms, for example benzyl alcohol, phenethyl alcohol, phenylpropyl alcohol, phenyloctadecyl alcohol and naphthyldecyl alcohol.

It is also possible to use polyols, in particular polyoxyethylene glycols such as ethylene glycols, diethylene glycol, triethylene glycol, propylene glycol and glycerol.

Preferred alcohols from those listed above are aliphatic or cycloaliphatic alcohols, preferably primary or secondary alcohols containing 1 to 4 carbon atoms, and cyclohexanol.

In a preferred variation of the process of the invention, a terpene alcohol is used, more particularly a terpene alcohol with formula (Va):

T—OH (Va)

in which formula (Va):

T represents a residue of a terpene alcohol containing multiples of 5 carbon atoms.

The term "terpene" as used in the present invention means oligomers derived from isoprene.

More precisely, the alcohol used has general formula (Va) where residue T represents a hydrocarbon group containing 5 to 40 carbon atoms, more particularly a linear or branched, saturated or unsaturated aliphatic group; or a monocyclic or polycyclic, saturated, unsaturated or aromatic cycloaliphatic group containing cycles containing 3 to 8 carbon atoms.

Without in any way limiting the scope of the invention, residue T can represent the residue of:

a linear or branched, saturated or unsaturated aliphatic terpene alcohol;

a saturated, unsaturated or aromatic, monocyclic cycloaliphatic terpene alcohol;

a polycyclic cycloaliphatic terpene alcohol comprising at least two saturated and/or unsaturated carbocycles.

If residue T is a linear or branched, saturated or unsaturated aliphatic terpene alcohol, the number of carbon atoms is in the range 5 to 40. More specific examples of residue T that can be mentioned are groups comprising 8 carbon atoms, saturated or with a double bond, and carrying methyl groups, preferably in the 3 and 7 position.

When a monocyclic compound is used, the number of carbon atoms in the cycle can vary widely from 3 to 8 carbon atoms, but is preferably 5 or 6 carbon atoms, usually carried by the aliphatic chain.

The carbocycle can be saturated or comprise 1 or 2 unsaturated bonds in the cycle, preferably 1 or 2 double bonds which are usually in the position α to the oxygen atom.

In the case of an aromatic terpene alcohol, the aromatic cycle is generally a benzene ring.

The compound can also be polycyclic, preferably bicyclic, meaning that at least two cycles have two carbon atoms in common. In the case of polycyclic compounds, the number of carbon atoms in each cycle is in the range 3 to 6: the total number of carbon atoms is preferably 7.

Examples of routine bicyclic structures are given below:

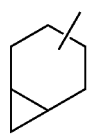
[4,1,0]

[2,2,1]

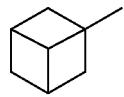
[3,1,1]

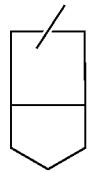
[3,2,0]

In the case of one cycle, the presence of substituents is not excluded provided that they are compatible with the envisaged application. The most common substituents to be carried by the carbocycle are one or more alkyl groups, preferably three methyl groups, a methylene group (corresponding to an exocyclic bond), or an alkenyl group, preferably an isopropen-yl group.

Examples of terpene alcohols that can be employee will now be cited:
saturated or unsaturated aliphatic terpene alcohols such as:
3,7-dimethyloctanol;
tetrahydro-allocimenol;
hydroxycitronellol;
1-hydroxy-3,7-dimethyl-7-octene;
nerol;
geraniol;
linalool;
citronellol;
3,7-dimethyloct-6-en-1-ol;
1-hydroxy-2-ethyl-5-isopropyl-8-methyl-2,7-nonadiene;
1-hydroxy-3,7,11-trimethyl-6,10-dodecadiene;
aromatic cycloaliphatic terpene alcohols such as:
thymol;
saturated or unsaturated, monocyclic or polycyclic cycloaliphatic terpene alcohols such as:
chrysanthemic alcohol;
1-hydroxyethyl-2,2,3-trimethylcyclopentane;
terpinol hydrate;
1,8-terpine;
dihydroterpineol;
β-terpineol;
perillyl alcohol;
1-methyl-3-hydroxy-4-isopropylcyclohexene;
α-terpineol;
terpinen-4-ol;
1,3,5-trimethyl-4-hydroxymethylcyclohexene;
carveol;
cis-2-pinanol;
cis-3-pinanol;
isoborneol;
verbenol;
trans-pinocarveol;
campholenic alcohol;
5-(2,3-dimethyltricyclo[2.2.1.0(2,6)]-hept-3-yl)-2-methyl-2-penten-1-ol, or santanol.
Of the alcohols cited above, preferred alcohols are:
chrysanthemic alcohol;
3,7-dimethyloctanol;
geraniol;
linalool;
citronellol;
hydroxycitronellol;
nerol;
thymol;
menthol;
isoborneol;
verbenol.

In accordance with the process of the invention, the etherification reaction is carried out in the presence of a catalyst constituted by a zeolite.

A natural or synthetic zeolite can be used; reference in this regard should be made to the description above.

In this step, preferred zeolites are mordenite, β or Y zeolites in the acid form.

The benzyl alcohol with formula (IV) can be reacted with the alkanol with formula (V) in the presence or absence of an organic solvent, one of the reactants possibly being used as a reaction solvent.

Preferably, the-alkanol is used as the reaction solvent, although other organic solvents can be used.

Non-limiting examples of suitable solvents that can be used are aliphatic, cycloaliphatic or aromatic ether-oxides, more particularly dipropyl oxide, diisopropyl oxide, dibutyl oxide, methyltertiobutyl ether, ethylene glycol dimethyl ether (glyme), diethylene glycol dimethyl ether (diglyme); phenyl oxide; dioxane or tetrahydrofuran (THF).

When the process is carried out batchwise, the catalyst can be present in an amount of 2% to 50%, preferably 5% to 20% with respect to the minor reactant. However, if the process is carried out continuously, for example by reacting a mixture of benzyl alcohol and alkanol on a fixed catalyst bed, these catalyst/benzyl alcohol ratios have no meaning and at a given moment there may be an excess weight of catalyst with respect to the starting benzyl alcohol.

The quantity of alkanol with formula (V), expressed as moles of alkanol per mole of benzyl alcohol with formula (IV), can also vary within wide limits. The mole ratio of alkanol with formula (V)/benzyl alcohol with formula (IV) can be in the range 1 to 30. The upper limit is not critical in nature, however for reasons of economy, there is no reason to exceed it.

The temperature of the etherification reaction can vary widely. It is advantageously in the range 50° C. to 200° C., more preferably in the range 50° C. to 100° C.

Generally, the reaction is carried out at atmospheric pressure but higher pressures of 1 to 50 bars, preferably 1 to 25 bars, are also suitable. Autogenous pressure is employed when the reaction temperature is higher than the boiling point of the reactants and/or products.

Preferably, the reaction is carried out under a controlled atmosphere of an inert gas such as nitrogen or rare gas such as argon.

The reaction period can vary widely. It is usually in the range 15 minutes to 10 hours, preferably in the range 30 minutes to 5 hours.

From a practical viewpoint, the process can be carried out continuously or batchwise.

In the first variation, the catalyst, alkanol preferably with formula (V), and optional organic solvent are charged then the benzyl alcohol, preferably with formula (IV), is introduced. In a preferred implementation, the benzyl alcohol is slowly introduced in fractions or continuously then the reaction mixture is heated to the desired temperature.

The other variation of the invention consists of carrying out the reaction continuously, in a tube reactor comprising the solid catalyst disposed in a fixed bed.

The benzyl alcohol and alkanol are preferably introduced separately.

They can also be introduced into a solvent as mentioned above.

The residence time for the material on the catalytic bed is, for example, between 15 min and 10 hours, preferably between 30 min and 5 hours.

At the end of the reaction, a liquid phase is recovered comprising etherified benzyl alcohol that can be recover conventionally.

The process of the invention produces etherified benzyl type alcohols preferably with formula (VI):

(VI)

in which R, $R_3$, $R_5$, A and n have the meanings defined above.

The process of the invention preferably produces the compound with formula (VI'):

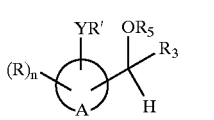

(VI')

in which R, R', $R_3$, $R_5$, Y, A and n have the meanings defined above.

More particularly, preferred compounds of the invention have formula (VIa):

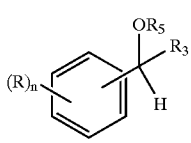

(VIa)

in which R, $R_3$, $R_5$ and n have the meanings defined above.

The process of the invention is particularly suitable for preparing mixed ethers i.e., ethers where group $R_5$ is different from the benzyl type group.

Examples will now be given. These examples are illustrative and are in no way limiting in nature.

In the examples, the degree of conversion and the yield obtained are defined.

The degree of conversion (TT) corresponds to the ratio between the number of moles of substrate transformed and the number of moles of substrate engaged.

The yield (RR) corresponds to the ratio between the number of moles of product formed and the number of moles of substrate engaged.

EXAMPLES

Step 1

Acetylation of veratrole

Example 1

100 g of acetoveratrole and 73.8 g of acetic anhydride were introduced into a 500 ml glass reactor.

It was stirred and 10 g of a catalyst comprising 60% of binder (silica) and 40% of a SPRAY-DRIED H-Y zeolite (Si/Al ratio of 15) was added.

It was heated to 90° C. and the temperature was maintained for 3 hours under those conditions.

The temperature was then brought back to 50° C. and filtration was carried out through sintered glass.

Gas chromatographic analysis was used to determine that the degree of veratrole transformation (TT) was 44% and the acetoveratrole yield (RR) was 43%.

Example 2

The above example was repeated, using a non-supported zeolite, namely 4 g of H-Y 720 zeolite from Zeolyst (Si/Al ratio of 15).

Gas chromatographic analysis was used to determine that the degree of veratrole transformation (TT) was 58% and the acetoveratrole yield (RR) was 55%.

Example 3

The above example was repeated, using a non-supported zeolite, namely 4 g of H-β CP 811 zeolite from Zeolyst (Si/Al ratio of 12.5).

Gas chromatographic analysis was used to determine that the degree of veratrole transformation (TT) was 36% and the acetoveratrole yield (RR) was 30%.

Example 4

40 g of a zeolitic catalyst in the form of extrudates containing 20% of alumina and 80% of a H-Y 712 zeolite (Si/Al ratio of 5.0) were charged into a 100 ml glass reactor.

400 g of veratrole and 147.6 g of acetic anhydride were added.

It was stirred and the mixture was continuously circulated over the fixed bed.

The reaction medium was then heated using a thermostatted bath to produce a constant temperature of 90° C. at the top of the catalytic bed.

These conditions were maintained, re-circulating the reaction mixture over the fixed bed for 5 hours.

Gas chromatographic analysis was used to determine that the degree of veratrole transformation (TT) was 17% and the acetoveratrole yield (RR) was 32%.

Example 5

44.2 g (0.32 mole) of veratrole, 16.4 g (0.161 mole) of acetic anhydride and 0.13 g (0.0008 mole) of anhydrous $FeCl_3$ were charged in that order into a 100 ml reactor.

The mixture was stirred for 30 minutes without heating.

The internal temperature rose to 30° C.

The reaction was continued for 2.5 hours, with stirring and heating to 110° C.

Gas chromatographic analysis showed that the reaction product contained 26.1 g of unreacted veratrole and 24.1 g of acetoveratrole, corresponding to a yield of 83%.

The acetoveratrole obtained was recovered conventionally by hydrolysis of the reaction medium, separation of the aqueous and organic phases and distillation of the organic phase.

Step 2

Acetoveratrole hydrogenation 50 g of acetoveratrole and 100 g of 96% ethyl alcohol were introduced into a 300 ml stainless steel reactor.

1.5 g of Raney nickel was added.

The reactor was purged with a stream of nitrogen and then with 2×10 bars of hydrogen.

The reactor was placed under a pressure of 10 bars of hydrogen, stirred and heated to 70° C.

The pressure in the reactor was kept constant at 10 bars throughout the reaction.

The conditions were maintained for 15 minutes following cessation of hydrogen consumption.

The reactor was then purged with 2×10 bars of nitrogen.

The catalyst was filtered off.

The solvent was then distilled.

49.8 g of a pale yellow oil was recovered.

Gas chromatographic analysis was used to determine that the degree of acetoveratrole transformation (TT) was 100% and the 1-(3,4-dimethoxyphenyl)ethanol yield (RR) was 98%.

Step 3

Etherification

Examples 1 to 5

The etherification reaction was carried out using different zeolitic catalysts, which were in the acid form.

In Examples 1 and 2, commercially available zeolites from PQ were used: a H-Y CBV 400 zeolite with a Si/Al ratio of 2.6 (Example 1) and a H-Y CBV 760 zeolite with a Si/Al ratio of 25 (Example 2).

Examples 3 and 4 used H-mordenite type zeolites: H-mordenite 20A with a Si/Al ratio of 10 (Example 3) and H-mordenite 90A with a Si/Al ratio of 45 (Example 4).

Example 5 used a H-β CBV 811 zeolite sold by PQ with a Si/Al ratio of 12.5.

100 g of 1-(3,4-dimethoxyphenyl)ethanol and 120 g of 2-butyn-1-ol were introduced into a stirred reactor.

It was stirred and 30 g of a zeolitic catalyst was added.

It was heated to 80° C.

After reacting for 4 hours, the reaction was terminated.

The catalyst was filtered off.

The results shown in Table (I) were obtained by gas chromatographic analysis.

The excess 2-butyne-1-ol was recovered by distillation.

TABLE (I)

| Examples | Zeolite | Si/Al | TT | RR ether |
|---|---|---|---|---|
| 1 | H—Y | 2.6 | 98 | 96 |
| 2 | H—Y | 25 | 99 | 18 |
| 3 | H-mordenite | 10 | 98 | 82 |
| 4 | H-mordenite | 45 | 98 | 82 |
| 5 | H-β | 12.5 | 100 | 85 |

Examples 6 to 10

The operating procedure of Examples 1 to 5 was repeated, this time using 200 g of 2-butyn-1-ol.

The following results were obtained

TABLE (II)

| Examples | Zeolite | Si/Al | TT | RR ether |
|---|---|---|---|---|
| 6 | H—Y | 2.6 | 100 | 98 |
| 7 | H—Y | 25 | 100 | 56 |
| 8 | H-mordenite | 10 | 100 | 93 |
| 9 | H-mordenite | 45 | 100 | 85 |
| 10 | H-β | 12.5 | 100 | 87 |

What is claimed is:

1. A process for preparing a benzyl ether compound from an aromatic compound, consisting of:
   in a first step, acylating an aromatic compound by reacting said aromatic compound with an acylation agent in the presence of an effective quantity of a zeolite or a Friedel-Crafts catalyst to produce a ketone compound comprising a carbonyl group,
   in a second step, reducing the carbonyl group to a carbinol group, to produce a benzyl alcohol compound comprising a hydroxyl group, and then
   in a third step, etherifying the hydroxyl group by reacting the benzyl alcohol compound with a further alcohol in the presence of a effective quantity of a zeolite.

2. A process according to claim 1, wherein the aromatic compound has general formula (I):

$$\text{A}\text{—(R)}_n \quad (I)$$

wherein:
   A represents the residue of a ring forming all or a portion of an aromatic, monocyclic or polycyclic, carbocyclic or heterocyclic system, said cyclic residue optionally carrying a group R representing a hydrogen atom or one or more identical or different substituents, and
   n represents the number of substituents on the ring.

3. A process according to claim 2, wherein residue A, which is optionally substituted, represents the a residue of:
   1) a monocyclic or polycyclic aromatic carbocyclic compound,
   2) a monocyclic or polycyclic aromatic heterocyclic compound, or
   3) a compound constituted by a concatenation of cycles, as defined in paragraphs 1) or 2), bonded together by:
      a covalent bond,
      an alkylene or alkylidene group comprising 1 to 4 carbon atoms, or
      one of the following groups:

—O—, —CO—, —COO—, —OCOO—,

—S—, —SO—, —SO$_2$—, —N—,
$\quad\quad\quad\quad\quad\quad\quad\quad\quad\quad\quad\quad\quad\quad\quad\;\; |$
$\quad\quad\quad\quad\quad\quad\quad\quad\quad\quad\quad\quad\quad\quad\quad\; R_0$ —CO—N—,
$\quad\quad\;\; |$
$\quad\quad\; R_0$ wherein $R_0$ represents a hydrogen atom, an alkyl group comprising 1 to 4 carbon atoms, a cyclohexyl group or a phenyl group.

4. A process according to claim 2, wherein residue A, which is optionally substituted, represents the a residue of a compound constituted by a concatenation of cycles, as defined in paragraphs 1) or 2), bonded together by a methylene or isopropylidene group.

5. A process according to claim 2, wherein group or groups R, which are identical or different, represent:
   a hydrogen atom;
   a linear or branched alkyl group;
   a linear or branched alkenyl group;
   a linear or branched halogenoalkyl group;
   a cycloalkyl group comprising 3 to 6 carbon atoms;
   a phenyl group;
   a benzyl group;
   a hydroxyl group;
   a NO$_2$ group;
   a $R_1$—O— alkoxy group or $R_1$—S— thioether groups wherein $R_1$ represents a linear or branched alkyl group comprising 1 to 6 carbon atoms;
   a phenoxy group;
   an alkenyloxy group;
   a —N—(R$_2$)$_2$ group, wherein groups R$_2$, which are identical or different, represent a hydrogen atom, a linear or branched alkyl group comprising 1 to 6 carbon atoms;
   a —NH—CO—R$_2$ group, where group R$_2$ has the meaning defined above;

carboxy groups;

a R₂—O—CO— group wherein group R₂ has the meaning defined above;

an acyloxy or aroyloxy group R₁—CO—O— wherein group R₁ has the meaning defined above;

a halogen atom; or a CF₃ group.

6. A process according to claim 2, wherein group or groups R, which are identical or different, represent:

a hydrogen atom;

a linear or branched alkyl group comprising 1 to 4 carbon atoms;

a linear or branched alkenyl group comprising 2 to 4 carbon atoms;

a linear or branched halogenoalkyl group comprising 1 to 4 carbon atoms and 1 to 9 halogen atoms;

a cyclohexyl group;

a phenyl group;

a benzyl group;

a hydroxyl group;

a NO₂ group;

a R₁—O— alkoxy group or R₁—S— thioether groups wherein R₁ represents a linear or branched alkyl group comprising 1 to 4 carbon atoms;

a phenoxy group;

an allyloxy group;

a —N—(R₂)₂ group, wherein groups R₂, which are identical or different, represent a hydrogen atom, a linear or branched alkyl group comprising 1 to 4 carbon atoms, or a phenyl group;

a —NH—CO—R₂ group, where group R₂ has the meaning defined above;

carboxy groups;

a R₂—O—CO— group wherein group R₂ has the meaning defined above;

an acyloxy or aroyloxy group R₁—CO—O— wherein group R₁ has the meaning defined above;

a fluorine atom; or a CF₃ group.

7. A process according to claim 2, wherein n is 2 or more, two groups R and the two successive atoms of the aromatic cycle being bonded together by an alkylene, alkenylene or alkenylidene group comprising 2 to 4 carbon atoms, to form a saturated, unsaturated or aromatic heterocycle comprising 5 to 7 carbon atoms, one or more carbon atoms being optionally replaced by a further oxygen or sulphur heteroatom.

8. A process according to claim 1, wherein the aromatic compound has general formula (Ia):

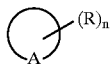

(Ia)

wherein:

A represents the residue of a cycle forming all or a portion of a monocyclic or polycyclic, aromatic carbocyclic or heterocyclic system, said cyclic residue optionally carrying a group R representing a hydrogen atom or one or more electron-donating substituents, which may be identical or different, and n represents the number of substituents on the cycle.

9. A process according to claim 8, wherein group or groups R, which are identical or different, represent:

a linear or branched alkyl group comprising 1 to 6 carbon atoms;

a linear or branched alkenyl group comprising 2 to 6 carbon atoms;

a cyclohexyl, phenyl or benzyl group;

a linear or branched alkoxy group comprising 1 to 6 carbon atoms;

an alkenyloxy group;

a phenoxy group;

a hydroxyl group;

a substituted amnino group, —N—(R₂)₂ wherein R₂ represent a hydrogen atom, a linear or branched alkyl group , or a phenyl group; or two groups R bonded together and forming alkylenedioxy or alkylenedithio groups.

10. A process according to claim 8, wherein group or groups R, which are identical or different, represent:

a methyl, ethyl, propyl, isopropyl, butyl, isobutyl, sec-butyl, or tert-butyl group;

a vinyl or allyl group;

a cyclohexyl, phenyl or benzyl group;

a methoxy, ethoxy, propoxy, isopropoxy, butoxy group;

an allyloxy group;

a phenoxy group;

a hydroxyl group;

a substituted amino group —N—(R₂)₂ wherein R₂ represent a hydrogen atom, a linear or branched alkyl group, or a phenyl group; or two groups R bonded together forming a methylenedioxy, ethylenedioxy, methylenedithio or ethylenedithio group.

11. A process according to claim 1, wherein the aromatic compound is an aromatic ether or thioether with general formula (I'):

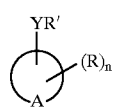

(I')

wherein

Y represents an oxygen atom or a sulphur atom;

A represents the residue of a cycle forming all or a portion of a monocyclic or polycyclic aromatic carbocyclic system comprising at least one YR' group, said residue optionally carrying one or a plurality of substituents;

R represents one or more substituents, which are identical or different;

R' represents a hydrocarbon group comprising 1 to 24 carbon atoms; and n is a number equal to 4 or less.

12. A process according to claim 11, wherein the aromatic compound is an aromatic ether or thioether with general formula (I'):

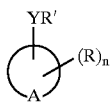 (I')

wherein:
Y represents an oxygen atom or a sulphur atom;
A represents the residue of a cycle forming all or a portion of a monocyclic or polycyclic aromatic carbocyclic system comprising at least one YR' group, said residue optionally carrying one or a plurality of substituents;
R represents one or more substituents, which are identical or different;
R' represents a hydrocarbon group comprising 1 to 24 carbon atoms which is a linear or branched, saturated or unsaturated acyclic aliphatic group; a saturated, unsaturated or aromatic, monocyclic or polycyclic cycloaliphatic group; or a linear or branched, saturated or unsaturated aliphatic group carrying a cyclic substituent; and
n is a number equal to 4 or less.

13. A process according to claim 11, wherein the aromatic compound is an aromatic ether or thioether with general formula (I'):

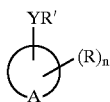 (I')

wherein:
Y represents an oxygen atom or a sulphur atom;
A represents the residue of a cycle forming all or a portion of a monocyclic or polycyclic aromatic carbocyclic system comprising at least one YR' group, said residue optionally carrying one or a plurality of substituents;
R represents one or more substituents, which are identical or different;
R' represents a hydrocarbon group comprising 1 to 24 carbon atoms;
R' and R form a cycle optionally comprising a further heteroatom; and
n is a number equal to 4 or less.

14. A process according to claim 11, wherein the aromatic ether or thioether has general formula (I') wherein R' represents:
a linear or branched, saturated or unsaturated acyclic aliphatic group, comprising 1 to 12 carbon atoms, with an hydrocarbon chain optionally being interrupted by a heteroatom or a functional group, or carrying substituents;
a linear or branched, saturated or unsaturated acyclic aliphatic group carrying a cyclic substituent, optionally substituted, said acyclic group being optionally bonded to the cycle by a covalent bond, a heteroatom or a functional group;
a carbocyclic group that is saturated or comprise 1 or 2 unsaturated bonds in the cycle, said cycle being optionally substituted; or
an aromatic carbocyclic group, said cycle being optionally substituted.

15. A process according to claim 11, wherein R' represents a methyl, ethyl or phenyl group.

16. A process according to claim 11, wherein residue A represents the residue of an aromatic monocyclic carbocyclic compound comprising at least 4 carbon atoms, or the residue of a polycyclic carbocyclic compound, said residue A optionally carrying one or more substituents on the aromatic nucleus.

17. A process according to claim 11, wherein the aromatic ether or thioether has formula (I'a):

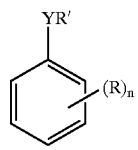 (I'a)

wherein:
n is a number equal to 4 or less;
Y represents an oxygen or sulphur atom;
group R' represents a linear or branched alkyl group comprising 1 to 6 carbon atoms; and
group or groups R, which are identical or different, represent:
a hydrogen atom;
a linear or branched alkyl;
a linear or branched alkenyl group;
a linear or branched halogenoalkyl group;
a cycloalkyl group comprising 3 to 6 carbon atoms;
a phenyl group;
a benzyl group;
a hydroxyl group;
a $NO_2$ group;
a $R_1$—O— alkoxy group or $R_1$—S— thioether groups wherein $R_1$ represents a linear or branched alkyl group comprising 1 to 6 carbon atoms;
a phenoxy group;
an alkenyloxy group;
a —N—$(R_2)_2$ group, wherein groups $R_2$, which are identical or different, represent a hydrogen atom, a linear or branched alkyl group comprising 1 to 6 carbon atoms;
a —NH—CO—$R_2$ group, where group $R_2$ has the meaning defined above;
carboxy groups;
a $R_2$—O—CO— group wherein group $R_2$ has the meaning defined above;
an acyloxy or aroyloxy group $R_1$—CO—O— wherein group $R_1$ has the meaning defined above;
a halogen atom; or
a $CF_3$ group.

18. A process according to claim 11, wherein the aromatic ether or thioether has formula (I'a):

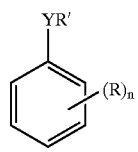 (I'a)

wherein:
n is a number equal to 0 or 1;
Y represents an oxygen or sulphur atom;

group R' represents a methyl, ethyl, propyl, isopropyl, butyl, isobutyl, sec-butyl, tert-butyl, or phenyl group; and group or groups R, which are identical or different, represent:
a hydrogen atom;
a linear or branched alkyl group comprising 1 to 4 carbon atoms;
a linear or branched alkenyl group comprising 2 to 4 carbon atoms;
a linear or branched halogenoalkyl group comprising 1 to 4 carbon atoms and 1 to 9 halogen atoms;
a cyclohexyl group;
a phenyl group;
a benzyl group;
a hydroxyl group;
a $NO_2$ group;
a $R_1$—O— alkoxy group or $R_1$—S— thioether groups wherein $R_1$ represents a linear or branched alkyl group comprising 1 to 4 carbon atoms;
a phenoxy group;
an allyloxy group;
a —N—$(R_2)_2$ group, wherein groups $R_2$, which are identical or different, represent a hydrogen atom, a linear or branched alkyl group comprising 1 to 4 carbon atoms, or a phenyl group;
a —NH—CO—$R_2$ group, where group $R_2$ has the meaning defined above;
carboxy groups;
a $R_2$—O—CO— group wherein group $R_2$ has the meaning defined above;
an acyloxy or aroyloxy group $R_1$—CO—O— wherein group $R_1$ has the meaning defined above;
a fluorine atom; or
a $CF_3$ group.

19. A process according to claim 17, wherein R' and R are placed on two neighbouring carbon atoms, and form together with the carbon atoms carrying them a cycle containing 5 to 7 atoms, optionally comprising a further heteroatom.

20. A process according to claim 12, wherein n is 1 or more, and groups R' and R and two successive atoms on a benzene nucleus are bonded together and form an alkylene, alkenylene or alkenylidene group comprising 2 to 4 carbon atoms to form a saturated, unsaturated or aromatic heterocycle comprising 5 to 7 atoms wherein one or more carbon atoms is optionally replaced by a further oxygen or sulphur heteroatom.

21. A process according to claim 20, wherein groups YR' and R form a methylenedioxy, ethylenedioxy methylenedithio or ethylenedithio group.

22. A process according to claim 11, wherein:
n is 0 or 1;
R' represents a linear or branched alkyl group comprising 1 to 6 carbon atoms or a phenyl group;
R represents a linear or branched alkyl group comprising 1 to 6 carbon atoms, or a linear or branched alkoxy group comprising 1 to 4 carbon atoms; and
groups YR' and R form a methylenedioxy, ethylenedioxy, methylenedithio or ethylenedithio group.

23. A process according to claim 11, wherein:
n is 0 or 1;
R' represents a methyl or ethyl group;
R represents a methyl, ethyl, methoxy or ethoxy group group; and
groups YR' and R form a methylenedioxy, ethylenedioxy, methylenedithio or ethylenedithio group.

24. A process according to claim 1, wherein the aromatic compound is benzene, toluene, isobutylbenzene, anisole, phenetole, veratrole, 1,2-methylenedioxybenzene, 2-methoxynaphthalene or thioanisole.

25. A process according to claim 1, wherein the acylation agent is selected from the group consisting of carboxylic acids, halides of carboxylic acids, and anhydrides.

26. A process according to claim 25, wherein the acylation agent has formula (II):

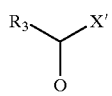

(II)

wherein:
$R_3$ represents a linear or branched, saturated or unsaturated aliphatic group comprising 1 to 24 carbon atoms; a monocyclic or polycyclic, saturated, unsaturated or aromatic cycloaliphatic group comprising 3 to 8 carbon atoms; or a linear or branched, saturated or unsaturated aliphatic group carrying a cyclic substituent; and
X' represents:
a halogen atom;
a hydroxyl group; or
a —O—CO—$R_4$ group, wherein $R_4$, which is identical to or different from $R_3$, has the same meaning as $R_3$; $R_3$ and $R_4$ optionally forming together a divalent, linear or branched, saturated or unsaturated, aliphatic group comprising at least 2 carbon atoms.

27. A process according to claim 26, wherein the halogen atom is a bromine or chlorine atom.

28. A process according to claim 26, wherein:
represents a chlorine atom; and
represents a linear or branched alkyl group comprising 1 to 12 carbon atoms, with a hydrocarbon chain optionally being interrupted by a heteroatom or by a functional group or carrying substituents; or $R_3$ represents a phenyl group.

29. A process according to claim 26, wherein X' represents a —O—CO—$R_4$ group wherein $R_3$ and $R_4$ are identical and represent an alkyl group comprising 1 to 4 carbon atoms, optionally carrying halogen atoms, or a phenyl group.

30. A process according to claim 26, wherein the acylation agent is selected from the group consisting in:
acetic anhydride;
propanoic anhydride;
butyric anhydride;
isobutyric anhydride;
trifluoroacetic anhydride;
benzoic anhydride;
monochloroacetyl anhydride;
dichloroacetyl anhydride;
acetyl chloride;
monochloroacetyl chloride;
dichloroacetyl chloride;
propanoyl chloride;
isobutanoyl chloride;
pivaloyl chloride;
stearoyl chloride;
crotonyl chloride;
benzoyl chloride;

chlorobenzoyl chlorides;
p-nitrobenzoyl chloride;
methoxybenzoyl chloride;
naphthoyl chloride;
acetic acid; and
benzoic acid.

31. A process according to claim 25, wherein the acylation agent is acetic anhydride, propanoic anhydride, benzoic anhydride, monochloroacetyl anhydride, dichloroacetyl anhydride or benzoyl chloride.

32. A process according to claim 1, wherein the zeolite is a synthetic zeolite selected from the group consisting in:
  unidimensional synthetic zeolites;
  two-dimensional zeolites;
  three-dimensional zeolites; and
  mesoporos MCM zeolite.

33. A process according to claim 1, wherein the zeolite is a synthetic zeolite selected from the group consisting of:
  ZSM-4, L zeolite, ZSM-12 zeolite, ZSM-22 zeolite, ZSM-23 zeolite or ZSM-48 zeolite;
  mordenite or ferrierite;
  β zeolite, Y zeolite, X zeolite, ZSM-5 zeolite, ZSM-11 zeolite or offretite; and
  mesoporos MCM zeolite.

34. A process according to claim 32, wherein the zeolite is a H-mordenite, a H-β zeolite, or a H-Y zeolite.

35. A process according to claim 1, wherein the zeolite is used alone or mixed with a mineral matrix.

36. A process according to claim 1, wherein the zeolite is used alone or mixed with an aluminum, silicon or zirconium oxide, or with a clay matrix.

37. A process according to claim 1, wherein the quantity of catalyst represents 0.01% to 50%, by weight with respect to the aromatic compound employed.

38. A process according to claim 37, wherein the quantity of catalyst represents 1.0% to 20%, by weight with respect to the aromatic compound employed.

39. A process according to claim 1, wherein the acylation reaction is carried out at a temperature in the range from 20° C. to 300° C.

40. A process according to claim 39, wherein the acylation reaction is carried out at a temperature in the range from 40° C. to 150° C.

41. A process according to claim 1, wherein the reaction mixtures traverse a catalytic bed.

42. A process according to claim 41, wherein reaction mixtures are returned in a mixing zone before being recycled for a number of times required to obtain a desired degree of conversion.

43. A process according to claim 42, wherein the degree of conversion is more than 20%.

44. A process according to claim 43, wherein the degree of conversion is in the range from 50% to 100%.

45. A process according to claim 1, wherein the catalyst is a salt comprising an organic counter-ion of metallic or metalloid elements from groups (IIIa), (IVa), (VIII), (IIb), (IIIb), (IVb), (Vb) and (VIb) of the periodic table.

46. A process according to claim 1, wherein the catalyst is a salt comprising an acetate, propionate, benzoate, methanesulphonate or trifluoromethanesulphonate of metallic or metalloid elements from groups (IIIa), (IVa), (VIII), (IIb), (IIIb), (IVb), (Vb) and (VIb) of the periodic table.

47. A process according to claim 1, wherein the catalyst is a salt comprising an organic counter-ion of a rare earth, or bismuth trifluoromethanesulphonate.

48. A process according to claim 1, wherein the catalyst is a salt comprising an inorganic counter-ion of metallic or metalloid elements from groups (IIa), (IIIa), (IVa), (VIII), (IIb), (IIIb), (IVb), (Vb) and (VIb) of the periodic table.

49. A process according to claim 1, wherein the catalyst is a salt comprising an a chloride, bromide, iodide, sulphate or oxide of metallic or metalloid elements from groups (IIa), (IIIa), (IVa), (VIII), (IIb), (IIIb), (IVb), (Vb) and (VIb) of the periodic table.

50. A process according to claim 48, wherein the catalyst is selected from the group consisting of magnesium chloride, aluminum chloride, aluminum bromide, ferric chloride, stannic chloride and boron trifluoride.

51. A process according to claim 26, wherein the quantity of catalyst is such that the ratio between the number of moles of catalyst and the number of moles of compound with formula (II) is in the range from 0.001 to 2.0.

52. A process according to claim 51, wherein the quantity of catalyst is such that the ratio between the number of moles of catalyst and the number of moles of compound with formula (II) is in the range from 0.05 to 1.0.

53. A process according to claim 45, wherein the acylation reaction is carried out at temperature in the range from 20° C. to 200° C.

54. A process according to claim 53, wherein the acylation reaction is carried out at temperature in the range from 40° C. to 120° C.

55. A process according to claim 26, wherein the ketone compound obtained has general formula (III):

wherein: $R_3$ and n have the meanings defined above in claim 26,

A represents the residue of a ring forming all or a portion of an aromatic, monocyclic or polycyclic, carbocyclic or heterocyclic system, said cyclic residue optionally carrying a group R representing a hydrogen atom or one or more identical or different substituents.

56. A process according to claim 11, wherein the ketone compound has formula (III'):

wherein R, R', Y, A and n have the meanings defined in claim 11, and $R_3$ represents a linear or branched, saturated or unsaturated aliphatic group comprising 1 to 24 carbon atoms; a monocyclic or polycyclic, saturated, unsaturated or aromatic cycloaliphatic group comprising 3 to 8 carbon atoms; or a linear or branched, saturated or unsaturated aliphatic group carrying a cyclic substituent.

57. A process according claim 17, wherein the ketone compound has formula (IIIa):

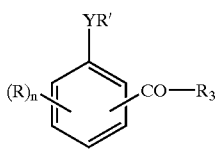

(IIIa)

wherein R, R', Y, and n have the meanings defined in claim 17, and

R₃ represents a linear or branched, saturated or unsaturated aliphatic group comprising 1 to 24 carbon atoms; a monocyclic or polycyclic, saturated, unsaturated or aromatic cycloaliphatic group comprising 3 to 8 carbon atoms; or a linear or branched, saturated or unsaturated aliphatic group carrying a cyclic substituent.

58. A process according to claim 1, wherein the ketone compound is hydrogenated in the presence of a catalyst comprising a metal from group VIII of the periodic table.

59. A process according to claim 1, wherein the ketone compound is hydrogenated in the presence of a catalyst comprising a noble metal, cobalt or nickel.

60. A process according to claim 59, wherein catalyst is Raney nickel.

61. A process according to claim 58, wherein the ketone compound is hydrogenated at a temperature in the range from 50° C. to 120° C.

62. A process according to claim 61, wherein the ketone compound is hydrogenated at a temperature in the range from 60° C. to 100° C.

63. A process according to claim 58, wherein hydrogenation is carried out in a liquid phase in the presence or absence of an organic solvent.

64. A process according to claim 26, wherein the benzyl alcohol compound obtained has formula (IV):

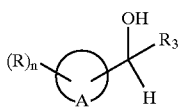

(IV)

wherein R₃ has the meanings defined above in claim 26,

A represents the residue of a ring forming all or a portion of an aromatic, monocyclic or polycyclic, carbocyclic or heterocyclic system, said cyclic residue optionally carrying a group R representing a hydrogen atom or one or more identical or different substituents, and n represents the number of substituents on the ring.

65. A process according to claim 11, wherein the benzyl alcohol compound obtained has formula (IV'):

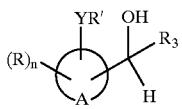

(IV')

wherein R, R', Y, A and n have the meanings defined in claim 11, and

R₃ represents a linear or branched, saturated or unsaturated aliphatic group comprising 1 to 24 carbon atoms; a monocyclic or polycyclic, saturated, unsaturated or aromatic cycloaliphatic group comprising 3 to 8 carbon atoms; or a linear or branched, saturated or unsaturated aliphatic group carrying a cyclic substituent.

66. A process according to claim 17, wherein the benzyl alcohol compound obtained has formula (IVa):

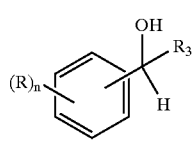

(IVa)

wherein R, and n have the meanings in claim 17, and

R₃ represents a linear or branched, saturated or unsaturated aliphatic group comprising 1 to 24 carbon atoms; a monocyclic or polycyclic, saturated, unsaturated or aromatic cycloaliphatic group comprising 3 to 8 carbon atoms;

or a linear or branched, saturated or unsaturated aliphatic group carrying a cyclic substituent.

67. A process according to claim 1, wherein an enantioselective hydrogenation of the ketone compound is carried out in the presence of a metal complex comprising an optically active diphosphine.

68. A process according to claim 67, wherein the optically active diphosphine is BINAP or BIPNOR [bis-(1-phospha-2,3-diphenyl-4,5-dimethylnorbornadiene)].

69. A process according to claim 1, wherein the benzyl alcohol compound is etherified by reacting it with a further alcohol in the presence of an effective quantity of a zeolite.

70. A process according to claim 69, wherein the benzyl alcohol compound is selected from the group consisting of:
vanillic alcohol;
p-hydroxybenzyl alcohol;
1-(4-hydroxy-3-methoxyphenyl)ethanol;
2-hydroxybenzyl alcohol;
p-methoxybenzyl alcohol;
3,4-dimethoxybenzyl alcohol;
6-n-propyl-3,4-dimethoxybenzyl alcohol;
(3,4-dimethoxyphenyl)dimethylcarbinol;
1-(3,4-dimethoxyphenyl)ethanol;
1-[1-hydroxy-2-methylpropyl]-3,4-dimethoxybenzene;
1-[1-hydroxy-2-methylpropyl]-3,4-diethoxybenzene;
1-[1-hydroxyethyl]-3,4-diethoxybenzene;
1-[1-hydroxyethyl]-3,4-dimethoxy-6-propylbenzene;
5-[1-hydroxyethyl]-1,3-benzodioxol; and
naphthalene-2-methylol.

71. A process according to claim 69, wherein the alcohol is an alkanol has general formula (V):

R₅—OH (V)

wherein R₅ represents a hydrocarbon comprising 1 to 24 carbon atoms.

72. A process according to claim 71, wherein the alkanol has formula (V) wherein R₅ represents:

a linear or branched, saturated or unsaturated, acyclic aliphatic group, with a hydrocarbon chain optionally being interrupted by a functional group or carrying substituents;

a linear or branched, saturated or unsaturated acyclic aliphatic group carrying a cyclic substituent that is optioanlly substituted, said acyclic group being optinally bonded to the cycle by a covalent bond, a heteroatom or a functional group; or a carbocyclic group that is saturated or contains 1 or 2 unsaturated bonds in the cycle, said cycle being optionally substituted.

73. A process according to claim 71, wherein the alkanol is a terpene alcohol of formula (Va):

T—OH (Va), wherein T represents a residue of a terpene alcohol comprising multiples of 5 carbon atoms.

74. A process according to claim 73, wherein the terpene alcohol has general formula (Va) wherein residue T represents a hydrocarbon group comprising 5 to 40 carbon atoms, and is a linear or branched, saturated or unsaturated aliphatic group, or a monocyclic or polycyclic, saturated, unsaturated or aromatic cycloaliphatic group comprising cycles comprising 3 to 8 carbon atoms.

75. A process according to claim 73, wherein residue T represents the residue of:
- a linear or branched, saturated or unsaturated aliphatic terpene alcohol;
- a saturated, unsaturated or aromatic, monocyclic cycloaliphatic terpene alcohol; or
- a polycyclic cycloaliphatic terpene alcohol comprising at least two saturated or unsaturated carbocycles.

76. A process according to claim 71, wherein the alcohol with formula (V) is selected from the group consisting of:
- methanol;
- ethanol;
- trifluoroethanol;
- propanol, isopropyl alcohol;
- butanol, isobutyl alcohol, sec-butyl alcohol, tert-butyl alcohol;
- pentanol, isopentyl alcohol, sec-pentyl alcohol and tert-pentyl alcohol;
- propargyl alcohol;
- 3-chlorobut-2-en-1-ol;
- 2-butyn-1-ol;
- 3,7-dimethyloct-6-en-1-ol;
- chrysanthemic alcohol;
- 3,7-dimethyloctanol;
- geraniol;
- linalool;
- citronellol;
- hydroxycitronellol;
- nerol;
- thymol;
- menthol;
- isoborneol; and
- verbenol.

77. A process according to claim 69, wherein the catalyst is a synthetic zeolite.

78. A process according to claim 69, wherein the alcohol is an alkanol, and the number of moles of alkanol is such that the ratio between the number of moles of alkanol and the number of moles of benzyl alcohol compound is in the range from 1 to 30.

79. A process according to claim 69, wherein the etherification reaction is carried out at a temperature in the range from 50° C. to 200° C.

80. A process according to claim 79, wherein the etherification reaction is carried out at a temperature in the range from 50° C. to 100° C.

81. A process according to claim 69, wherein a catalytic bed is used, with a the residence time for material flux on the catalytic bed being in the range from 15 min to 10 h.

82. A process according to claim 69, wherein a catalytic bed is used, with a the residence time for material flux on the catalytic bed being in the range from 30 min to 5 h.

83. A process according to claim 69, wherein at the end of the reaction, a liquid phase is obtained, comprising an etherified benzyl alcohol compound, which is then recovered conventionally.

84. A process according to claim 71, wherein the etherified benzyl alcohol compound obtained has formula (VI):

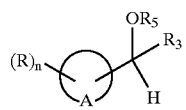

(VI)

wherein $R_5$, has the meanings given in claim 71, $R_3$ represents a linear or branched, saturated or unsaturated aliphatic group comprising 1 to 24 carbon atoms; a monocyclic or polycyclic, saturated, unsaturated or aromatic cycloaliphatic group comprising 3 to 8 carbon atoms;

or a linear or branched, saturated or unsaturated aliphatic group carrying a cyclic substituent, A represents the residue of a ring forming all or a portion of an aromatic, monocyclic or polycyclic, carbocyclic or heterocyclic system, said cyclic residue optionally carrying a group R representing a hydrogen atom or one or more identical or different substituents, and n represents the number of substituents on the ring.

85. A process according to claim 71, wherein the etherified benzyl alcohol compound obtained has formula (VI'):

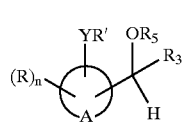

(VI')

wherein $R_5$ has the meanings given in claim 71, $R_3$ represents a linear or branched, saturated or unsaturated aliphatic group comprising 1 to 24 carbon atoms; a monocyclic or polycyclic, saturated, unsaturated or aromatic cycloaliphatic group comprising 3 to 8 carbon atoms; or a linear or branched, saturated or unsaturated aliphatic group carrying a cyclic substituent, Y represents an oxygen atom or a sulphur atom, R' represents a hydrocarbon group comprising 1 to 24 carbon atoms, A represents the residue of a ring forming all or a portion of an aromatic, monocyclic or polycyclic, carbocyclic or heterocyclic system, said cyclic residue optionally carrying a group R representing a hydrogen atom or one or more identical or different substituents, and n represents the number of substituents on the ring.

86. A process according to claim 71, wherein the etherified benzyl alcohol compound obtained has formula (VIa):

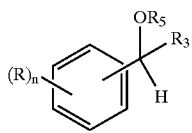 (VIa)

wherein $R_5$ has the meanings given in claim 71, $R_3$ represents a linear or branched, saturated or unsaturated aliphatic group comprising 1 to 24 carbon atoms;

a monocyclic or polycyclic, saturated, unsaturated or aromatic cycloaliphatic group comprising 3 to 8 carbon atoms;

or a linear or branched, saturated or unsaturated aliphatic group carrying a cyclic substituent, R represents a hydrogen atom or one or more identical or different substituents, and n represents the number of substituents on the ring.

* * * * *